United States Patent [19]

Eoga

[11] 4,405,486
[45] Sep. 20, 1983

[54] METHOD FOR PREPARING GRANULATED PERBORATE SALTS CONTAINING A POLYMERIC FLUOROCARBON

[75] Inventor: Anthony B. J. Eoga, Boonton, N.J.

[73] Assignee: Warner-Lambert Company, Morris Plains, N.J.

[21] Appl. No.: 380,164

[22] Filed: May 20, 1982

Related U.S. Application Data

[63] Continuation-in-part of Ser. No. 297,892, Aug. 31, 1981, Pat. No. 4,362,639, which is a continuation-in-part of Ser. No. 251,030, Apr. 3, 1981.

[51] Int. Cl.$^3$ .............................. B01J 2/22; B01J 2/28; C11D 7/28; C11D 7/54
[52] U.S. Cl. ........................ 252/186.31; 23/313 R; 252/99; 252/174; 252/174.23; 252/DIG. 2; 252/DIG. 3; 264/118; 264/122
[58] Field of Search ............... 264/117, 118, 120, 122, 264/127; 23/313 R; 252/186.3, 186.31, 99, 174, 174.23, DIG. 2, DIG. 3

[56] References Cited

U.S. PATENT DOCUMENTS

| | | | |
|---|---|---|---|
| 3,227,790 | 1/1966 | Bretschneider | 264/117 |
| 3,337,466 | 8/1967 | Puetzer | 252/99 |
| 3,340,152 | 9/1967 | Hotko | 424/35 |
| 3,458,446 | 7/1969 | Diaz | 252/99 |
| 3,558,497 | 1/1971 | Lawes | 252/99 |
| 3,704,227 | 11/1972 | Hill | 252/95 |
| 3,928,524 | 12/1975 | Leverett | 264/117 |

*Primary Examiner*—Dennis L. Albrecht
*Attorney, Agent, or Firm*—Daniel A. Scola, Jr.; Stephen Raines

[57] ABSTRACT

A method is disclosed for the preparation of granulated perborate salts having improved utility in compressible compositions such as those formed into denture cleanser tablets. The method broadly comprises forming a mixture of one or more perborate salts such as sodium perborate monohydrate and anhydrous sodium perborate, with a polymeric fluorocarbon such as polytetrafluoroethylene, with the polytetrafluoroethylene present in an amount ranging from about 0.01% to about 0.70% by weight of the perborate salt. The particles thus prepared exhibit combination of improved hardness and specific weight that facilitates their participation in the compressible cleanser composition, together with enhanced disintegration characteristics that are favorably imparted to the cleanser tablets.

The present invention also includes the granular salts prepared by the method, which have a broad range of utility in detergents, cleansers and the like.

18 Claims, No Drawings

METHOD FOR PREPARING GRANULATED PERBORATE SALTS CONTAINING A POLYMERIC FLUOROCARBON

CROSS-REFERENCE TO RELATED APPLICATIONS

The present application is a continuation-in-part of my copending application Ser. No. 297,892, filed Aug. 31, 1981, now U.S. Pat. No. 4,362,639, which is in turn a continuation-in-part of my copending application Ser. No. 251,030, filed Apr. 3, 1981.

BACKGROUND OF THE INVENTION

1. Field of the Invention

The present invention relates to the preparation of granulated materials, and more particularly to the preparation of granulated perborate salts, such as anhydrous sodium perborate, as well as to the granules thus obtained.

2. Description of the Prior Art

Perborate salts such as sodium perborate monohydrate, and sodium perborate anhydrous have enjoyed broad use in the preparation of a variety of cleansing compositions, and particularly as ingredients in denture cleansers. The perborate salts are popular because of their elevated active oxygen content and temperature stability.

Generally, anhydrous sodium perborate, of the grade and texture utilized in the preparation of denture cleansing tablets, is a fluffy material of low specific weight. These properties impede the rapid and successful preparation of compressed cleanser tablets, and the tablets so prepared frequently fracture or disintegrate. Previous efforts to increase the specific weight of anhydrous sodium perborate, to make it more compressible and thereby a more manageable tableting ingredient, have failed, and prior art efforts in this regard have relied primarily upon the addition to the entire cleansing composition of one or more tableting aids such as talc, sodium benzoate, and the like. These ingredients, however, have certain drawbacks, particularly in the instance where the tablet activity is a function of its speed of disintegration in a liquid such as water. In such instance, the tableting aids tend to prolong the disintegration time of the tablet, with the result that the activity of the tablet is delayed, and the tablet is less attractive to the consumer.

A process is disclosed in U.S. Pat. No. 4,115,519 to Brichard et al., for the manufacture of sodium perborate monohydrate, that purportedly results in the preparation of granules of the monohydrate possessing the desired particle size, specific weight, abrasion resistance and flowability sought for use in connection with the compaction of dental cleanser tablets. The technique disclosed by the patent, however, is complex and costly, and requires specialized apparatus to conduct a fluidized bed particle formation in contact with hydrogen peroxide. The patentees refer to prior art processes for the formation of the monohydrate salt, and indicate that those processes, as well, are complex and expensive, and frequently yield particles that are unsuitable for the present applications.

U.S. Pat. No. 3,340,152, to Hotko, discloses that polyfluorocarbons may be utilized in the manufacture of tablets, as lubricants, and in amounts by weight of the tableting composition, ranging from about 1% to about 15% by weight, to supplant such known lubricants as magnesium stearate, sodium lauryl sulfate, polyethylene glycols and the like. Hotko suggests that the fluoropolymer may be added directly to the tableting mixture, in its capacity and amount as a lubricant, and purportedly has a favorable effect on the tablet-forming process. There is no disclosure in Hotko that the fluoropolymers would serve as agglomeration or compaction aids, to facilitate the preparation of granulated materials of increased and improved specific weight.

A need therefore exists for a method and associated granular product, that provides the perborate salts, and in particular, anhydrous sodium perborate, in a form that is easily and efficiently compressed in combination with other ingredients of a tablet-forming cleanser composition.

SUMMARY OF THE INVENTION

In accordance with the present invention, a method for preparing perborate salts in granular form is disclosed, which comprises forming a mixture of the perborate salt in the dried condition, with a polymeric fluorocarbon, the fluorocarbon present in an amount by weight of the perborate salt, ranging from about 0.01% to about 0.70%. This mixture is then compacted to provide a plurality of preforms, which are then comminuted under agitation to form the granulate. The granulate may have a particle size capable of passing through a 30 mesh screen.

Preferably, the perborate salts may be selected from sodium perborate monohydrate, and anhydrous sodium perborate, with anhydrous sodium perborate preferred. The polymeric fluorocarbon may be selected from a variety of well known non-toxic materials, with polytetrafluoroethylene preferred. The polymeric fluorocarbon may be present in an amount preferably ranging from about 0.33% to about 0.66% by weight of the perborate salt. The mixture of polymeric fluorocarbon and perborate salt may be compacted by passage through a roller compactor to form preforms such as flakes, or by slugging, with the preforms preferably achieving a hardness on the order of 20 to 25 kg/in$^2$. The preforms are thereafter comminuted, by, for example, passage through an oscillating granulator, and are reduced to granules having particle sizes ranging preferably from about 16 to about 30 mesh, and most preferably up to about 16 mesh.

The present invention also includes the granules prepared by this process, comprising the perborate salt in admixture with a polymeric fluorocarbon, the fluorocarbon present in amounts of from about 0.01% to about 0.70% by weight of the perborate salt, and preferably from about 0.33% to about 0.66% by weight. The granules prepared by the present process have particular utility in the instance where they are included in moldable cleanser compositions, such as denture cleansers that are compressed into tablet form for commercial use. The granules of the present invention are particularly noteworthy, in that they remain cohesive and provide sufficient density and specific weight for the perborate salt, to permit efficient and rapid handling of the perborate salt, particularly in the instance where anhydrous sodium perborate is involved.

The present method is simply practiced, and does not require complex processing, machinery or large amounts of energy input.

Accordingly, it is a principal object of the present invention to provide a method for the granulation of perborate salts to render them better suited for incorporation into moldable cleanser compositions.

It is a further object of the present invention to provide a method as aforesaid that is simple and economical to practice.

It is a still further object of the present invention to provide a method as aforesaid that provides a granulated perborate salt product that is mechanically stable.

It is a still further object of the present invention to provide perborate salts in granulated form by a simplified method of preparation.

Other objects and advantages will become apparent to those skilled in the art from a review of the ensuing detailed description.

DETAILED DESCRIPTION

The present invention relates to a method for granulated perborate salts to render them more amenable to mechanical forming such as compression, when they are incorporated in moldable compositions such as cleansers pressed into tablet form. The method comprises mixing a quantity of powdered perborate salt, such as sodium perborate monohydrate or anhydrous sodium perborate, with a compression aid comprising a polymeric fluorocarbon, the polymeric fluorocarbon present in an amount by weight of the perborate salt, of from about 0.01% to about 0.70%, and preferably from about 0.33% to about 0.66%.

The polymeric fluorocarbon may be selected from a well known group of polymeric and copolymeric substances made up of carbon and fluorine, which, in addition, may contain hydrogen and/or chlorine. The fluorocarbons may include at least one fluoroolefin; for example, polytetrafluoroethylene, and copolymers of tetrafluoroethylene and hexafluoropropylene are contemplated. Also included would be polyvinylidene fluoride, a copolymer of vinylidene fluoride and hexafluoropropylene, as well as other polymeric fluorocarbons recited in U.S. Pat. No. 3,340,152 to Hotko, the pertinent disclosure of which is incorporated herein by reference.

The fluorocarbon polymers may be utilized in the present invention, in the form of powders having particle sizes acceptable for combination with the present perborate salts, and preferably ranging up to about 150 microns in size. The exact particle size may vary with an average particle size of 25 to 75 microns commonplace. The exact particle size is not critical to the practice of the present invention.

After the mixture of the perborate salt and the polymeric fluorocarbon has been prepared, the resulting mixture may be compacted to form a plurality of cohesive preforms. In particular, compaction may be conducted on a continuous or batch process, whereby the designated amount of the fluorocarbon polymer is added to a continuous stream of the perborate salt, and this stream is thereafter roller compacted in dry form to form flakes of the mixture. Alternately, formation of the preforms may be achieved by the slugging method, whereby the mixture is agglomerated by compression in, for example, a tablet slugging press, to form a plurality of slugs. The preforms, whether flakes or slugs, may be prepared to a hardness ranging from about 5 kg/in$^2$ to about 30 kg/in$^2$ or greater, depending upon the intended use of the granules. For example, in the instance where the granulate is to be employed in a composition for compression into denture cleanser tablets, the slug may have a hardness value of from about 20 to about 30 kg/in$^2$, and will successfully participate in subsequent tableting operations. The exact hardness of the granulate is not limited, however, and the foregoing range is presented for purposes of illustration only.

Subsequent to their formation, the preforms are comminuted or reduced to the granules of the present invention, by, for example, passage through a suitable oscillating granulator, or other apparatus capable of forming granules from the preforms. Thus, compactor mills, grinders and other similar well known apparatus may be utilized to reduce the particle size of the preforms to the end size desired.

The resulting granules may be prepared to a variety of particle sizes, and in particular, may be prepared to a size not exceeding that capable of passing through a 30 mesh screen. Preferably, and in the instance where the granules of the present invention are to be added as a component to a composition to be compressed into a cleanser tablet, the particle sizes may preferably range from about 16 to about 30 mesh, and may preferably range from about 16 to about 20 mesh. The specific mesh size may naturally vary, as indicated earlier.

The particular advantage of the present invention resides in the fact that the material being granulated, i.e. the perborate salts, and specifically anhydrous sodium perborate, are extremely difficult to process as they are generally commercially available as a fluffy powder having very low specific weight. Prior art attempts to incorporate the anhydrous sodium perborate into compositions that are thereafter molded by compression, have relied upon the addition of conventional tableting aids in exceedingly large amounts, that have adversely effected the performance of the cleanser tablets. For example, granules were prepared in accordance with the teachings of the U.S. patent to Hotko, cited earlier and incorporated herein by reference, which teaches the presence of the polymeric fluorocarbons in amounts ranging from about 1% to about 15% by weight, and preferably from about 2% to about 10% by weight of the composition. The tablets prepared utilizing the teachings of Hotko, were found however to exhibit undesirable delay in disintegration time, which is crucial to the commercial acceptability and cleaning effectiveness of the tablets, in the instance where denture cleanser tablets are prepared.

By contrast, the preparation of the granules in accordance with the present invention, i.e. with the polymeric fluorocarbon present within a maximum amount of 0.70% by weight of the perborate salt, confers the desirable qualities of compactability, cohesion and performance that are actually improved over conventional preparations. The perborate salt granules of the present invention are therefore broadly useful in all instances where the combination of particle strength and stability, and enhanced speed of disintegration are required.

The present invention will be better understood from a consideration of the following illustrative examples.

EXAMPLE I

A quantity of anhydrous sodium perborate obtained as a fluffy powder, was prepared in a container, to which was added a quantity of polytetrafluoroethylene powder identified as Grade F5A by the E. I. duPont DeNemours & Co., Inc. In this experiment, 540 grams of the perborate were mixed with 3.25 grams of the polytetrafluoroethylene. Blending was conducted for approximately 3 minutes, after which the mixture was compressed to a hardness of 15 kg/in$^2$ with a tablet slugging press having 27/32" tablet dies. Thereafter, the slugs were passed through an oscillating granulator having a 16 mesh screen, so that granules of the mixture of anhydrous sodium perborate and polytetrafluoroethylene were obtained having a particle size of 16 mesh.

EXAMPLE II

The procedure outlined in Example I was repeated, with the exception that 750.0 grams of anhydrous sodium perborate and 1.0 gram of polytetrafluoroethylene were combined. The resulting granules maintained a comparable hardness to those prepared in Example I.

EXAMPLE III

A denture cleansing composition was prepared incorporating a granulate of anhydrous sodium perborate and polytetrafluoroethylene powder, prepared in accordance with the method of the present invention, as illustrated in Examples I and II. The specific ingredients of the denture cleansing composition, including the weight amounts of the respective components of the granulate, are set forth in Table I, below.

TABLE I

| DENTURE CLEANSING COMPOSITION | |
|---|---|
| INGREDIENT | AMOUNT (GRAMS) |
| Sodium Perborate Monohydrate | 2865.0 g |
| Trisodium Phosphate | 2094.0 g |
| FD&C Green #3 | 2.85 |
| FD&C Blue #1 Lake Lakolene B3016 | 17.1 |
| Sodium Meta Silicate (Fines-Drymet) | 1419.0 |
| Sodium Perborate Anhydrous | 1704.0 |
| Polytetrafluoroethylene Powder | 27.9 |
| Ethylenediaminetetraacetic Acid TetraSodium Salt Dihydrate/Pure | 225.0 |
| Brazilian Mint, Encapsulated or Spray Dried | 45.0 |
| Sodium Perborate Special Powder | 90.0 |
| Detergent | 14.4 |
| Magnesium Stearate USP | 1.5 |

The above cleanser composition, including the anhydrous perborate granulate, was then mixed and pressed into 2500 tablets, in a tablet press having a tablet dye of 27/32". Each tablet weighed approximately 2.835 grams and had a hardness of approximately 20 kg/in$^2$ and 65 seconds. The tablets were approximately 0.207 inches thick and upon testing, were found to have available oxygen of 165 mg/tablet, with a disintegration time of 90 seconds in 102 milliliters of 45° C. water. The performance of these tablets was considered above average in the measured parameters, and tablets containing the perborate granulate were determined to be desirable for use in denture cleanser compositions in tablet form.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method for preparing a granulated perborate salt, comprising:
    A. forming a mixture of said perborate salt with a polymeric fluorocarbon, said mixture containing said polymeric fluorocarbon in an amount by weight of said perborate salt, of from about 0.01% to about 0.70%;
    B. compacting said mixture into a plurality of preforms; and
    C. comminuting said preforms under agitation, to form said granulated perborate salt.

2. The method of claim 1 wherein said perborate salt is selected from the group consisting of sodium perborate monohydrate, anhydrous sodium perborate and mixtures thereof.

3. The method of claim 2 wherein said perborate salt comprises anhydrous sodium perborate.

4. The method of claim 1 wherein said polymeric fluorocarbon includes at least one fluoroolefin.

5. The method of claim 4 wherein said polymeric fluorocarbon comprises polytetrafluoroethylene.

6. The method of claims 1, 4 or 5 wherein said polymeric fluorocarbon is present in an amount from about 0.33% to about 0.66% by weight.

7. The method of claim 1 wherein said mixture is compacted by passing through a roller compactor, and said preforms comprise flakes.

8. The method of claim 1 wherein said mixture is compacted by slugging.

9. The method of claim 1 wherein said preforms are comminuted by passage through an oscillating granulator, to a particle size passing through a 30 mesh screen.

10. A granulated perborate salt product, suitable for inclusion in a compactible composition, said product comprising a precompressed mixture of said perborate salt and from about 0.1% to about 0.70% of a polymeric fluorocarbon.

11. The product of claim 10 wherein said perborate salt is selected from the group consisting of sodium perborate monohydrate, anhydrous sodium perborate, and mixtures thereof.

12. The product of claim 10 wherein said perborate salt comprises anhydrous sodium perborate.

13. The product of claim 10 wherein said polymeric fluorocarbon includes at least one fluoroolefin.

14. The product of claim 10 wherein said polymeric fluorocarbon comprises polytetrafluoroethylene.

15. The product of claims 10-13 or 14 wherein said polymeric fluorocarbon is present in an amount of from about 0.33% to about 0.66% by weight.

16. The product of claim 10 having a hardness on the order of 30 kg/in$^2$.

17. The product of claim 10 having a hardness ranging from about 15 kg/in$^2$ to about 30 kg/in$^2$.

18. The product of claim 10 having a particle size capable of passing through a 30 mesh screen.

* * * * *